United States Patent [19]

Ackermann et al.

[11] Patent Number: 5,116,872
[45] Date of Patent: May 26, 1992

[54] MICROBICIDAL COMPOSITIONS

[75] Inventors: Peter Ackermann, Pfeffingen; Hanspeter Fischer, Bottmingen; Rolf Vogel, Reinach, all of Switzerland; Karlheinz Drauz, Freigericht; Hans-Albrecht Hasseberg, Rodenbach; Hans-Jochen Hasselbach, Gelnhausen; Günter Knaup, Bruchköbel; Hans-Peter Krimmer, Frankfurt; Matthias Schäfer, Obernburg, all of Fed. Rep. of Germany

[73] Assignees: Ciba-Geigy Corporation, Ardsley, N.Y.; Degussa Aktiengesellschaft, Frankfurt, Fed. Rep. of Germany

[21] Appl. No.: 643,882

[22] Filed: Jan. 22, 1991

[30] Foreign Application Priority Data

Jan. 24, 1990 [CH] Switzerland ............ 228/90

[51] Int. Cl.$^5$ ............ A01N 37/00; A01N 37/44; A01N 55/02; A01N 55/04
[52] U.S. Cl. ............ 514/561; 514/492; 514/493; 514/494; 514/499; 514/501; 514/502; 514/505; 514/529
[58] Field of Search ............ 514/492, 493, 494, 499, 514/501, 502, 505, 529, 561

[56] References Cited

U.S. PATENT DOCUMENTS 3,639,626  2/1972  Nagasawa et al. ............ 514/561
3,746,495  7/1973  Malis et al. ............ 429/319
5,037,809  8/1991  Miyauchi et al. ............ 514/561

OTHER PUBLICATIONS

Chemical Abstract, 80:13816x corresponding to JP-A2 73/11958.

Primary Examiner—Allen J. Robinson
Attorney, Agent, or Firm—Marla J. Mathias; Edward McC. Roberts

[57] ABSTRACT

1-Aminocyclohexanecarboxylic acid derivatives of the formula I

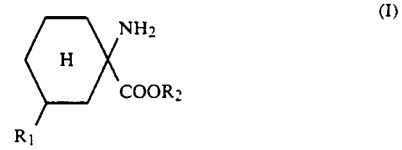

or their acid addition salts or a metal complex can be employed for protecting plants from microorganisms. In the formula I, $R_1$ is hydrogen or $C_1$-$C_4$ alkyl, $R_2$ is hydrogen, $C_1$-$C_6$ alkyl, benzyl, or an ammonium radical which is unsubstituted or substituted by hydrocarbon radicals having not more than 20 C atoms, or a metal ion equivalent.

Compounds of the formula I can be employed in the form of crop protection agents using suitable carrier materials.

8 Claims, No Drawings

MICROBICIDAL COMPOSITIONS

The present invention relates to compositions for controlling phytopathogenic fungi and for preventing fungal attack, and these compositions contain, as the active substance, at least one 1-aminocyclohexanecarboxylic acid derivative of the formula I

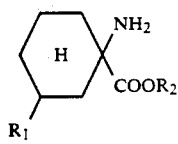

or an acid addition salt or a metal complex thereof, $R_1$ being hydrogen or $C_1$-$C_4$alkyl and $R_2$ being hydrogen, $C_1$-$C_6$alkyl, benzyl, or an ammonium radical which is unsubstituted or substituted by hydrocarbon radicals having not more than 20 C atoms, or being a metal ion equivalent, together with a phytophysiologically acceptable carrier material and, if desired, other dispersants. The invention furthermore relates to the appropriate use of the compounds of the formula I for protecting plants, parts of plants, or for protecting the propagation stock of the plants, in particular the seed.

Alkyl, here and in what follows, is understood as meaning, depending on the chain length, methyl, ethyl, propyl, butyl, pentyl, hexyl and their particular isomers, (for example isopropyl, sec-butyl, tert-butyl, isoamyl, neopentyl and the like).

Examples of salt-forming acids are inorganic acids (hydrohalic acids such as hydrochloric acid, hydrobromic acid, hydroiodic acid and a sulfuric acid, nitric acid or phosphoric acid) and organic acids such as acetic acid, difluorochloroacetic acid, trifluoroacetic acid, trichloroacetic acid, propionic acid, glycolic acid, thiocyanic acid, maleic acid, malic acid, lactic acid, succinic acid, citric acid, benzoic acid, cinnamic acid, oxalic acid, terephthalic acid, formic acid, benzenesulfonic acid, p-toluenesulfonic acid, methanesulfonic acid, salicylic acid, mandelic acid, p-aminosalicylic acid, 2-phenoxybenzoic acid, pyridine-3-sulfonic acid, nicotinic acid or 2-acetoxybenzoic acid.

Metal complexes of the formula I consist of the organic molecule on which they are based and an inorganic or organic metal salt, for example the halides, nitrates, sulfates, phosphates, acetates, trifluoroacetates, trichloroacetates, propionates, tartrates, sulfonates, salicylates, benzoates etc. of the elements of the first to fourth main group such as Na, Ca, Mg, aluminium, tin or lead, and of the elements of the first to eighth sub-groups such as chromium, manganese, iron, cobalt, nickel, copper, zinc, silver etc., preferably of the elements of the first, second and sixth to eighth sub-groups. The metals can here be present in the various valences which they can assume. The metal complexes of the formula I can contain one or more organic molecule moieties.

Metal salts of the formula I consist of the acid anion of the cyclic aminocarboxylic acid on which they are based and one metal cation, or several different ones, for example $Na^+/Fe^{3+}$; $Na^+/K^+$; $Ca^{++}/Mg^{++}$; $Cu^{++}/Ni^{++}/Mn^{++}/Co^{++}$ etcetera.

Salts of aliphatic amines of the formula I contain the acid anion of the cyclic aminocarboxylic acid on which they are based and the ammonium ion of an amine, for example $N(alkyl)_3$, $NH(alkyl)_2$, $NH_2(alkyl)$ and $N(CH_3)_3$, $N(C_2H_5)_3$, $NH(CH_3)_2$, $NH(C_3H_7\text{-}n)_2$, $N(benzyl)(C_6H_{13})_2$, $NH(C_3H_7\text{-}i)_2$, $NH_2(C_3H_7\text{-}i)$, $NH_2(CH_3)$, $NH_2(C_4H_9\text{-}n)$, $NH_2(cyclohexyl)$, $NH_2(C_6H_5)$, $NH_2CH_2CH_2C_6H_5$, $NH_2CH(C_6H_5)CH_3$, $^{\oplus}N(CH_3)_4$, $^{\oplus}N(CH_3)_3(benzyl)$ etcetera.

The compounds of the formula I are stable substances which have very good microbicidal properties and can be used against phytopathogenic fungi. Together with suitable carriers which are customary in agrochemistry, they can be used for preparing effective pesticides.

A preferred group of microbicides consists of compounds of the formula I in which $R_1$ is hydrogen or $C_1$-$C_3$alkyl and $R_2$ is hydrogen, $C_1$-$C_4$alkyl or an ammonium radical which is unsubstituted or substituted by hydrocarbon radicals having not more than 20 C atoms, or is the metal ion equivalent of one, two or more metal cations. These copounds will be named compound group Ia.

Preferred compounds amongst these are those in which $R_1$ is hydrogen, methyl, ethyl or isopropyl and $R_2$ is hydrogen, methyl, ethyl, propyl, isopropyl or an unsubstituted or substituted ammonium radical whose substituents are hydrogen, alkyl groups and 0 to 2 phenyl groups and/or benzyl groups, or is the metal ion equivalent of Li, Na, K, Mg, Ca, Cu, Mn, Zn, Sn, Fe, Ni, Co, Cr, Al, Ti, Zr or of two or more of these elements (=sub-group Ib). Particularly preferred compounds from amongst these are those in which $R_1$ is hydrogen (=sub-group Ic), and from amongst these, in turn, those in which $R_2$ is hydrogen or one, two or more of the metal ion equivalents mentioned (=sub-group Id), especially those in which $R_2$ is hydrogen or a metal ion equivalent of Na, K, Mg, Ca, Cu, Mn, Zn, Fe, Ni or Al (=sub-group Ie).

Another important compound group within the scope of sub-group Ib are those compounds in which $R_1$ is hydrogen and $R_2$ is hydrogen or $NH_4^+$, it being possible for all or some of its hydrogen atoms to be substituted by 0 to 1 phenyl or 0 to 1 benzyl and 4 to 1 alkyl groups having not more than 4 C atoms (=sub-group If), in particular those in which the alkyl groups are selected from amongst methyl, ethyl, propyl, isopropyl, butyl and tert-butyl (=sub-group Ig).

Examples of important individual compounds are 1-aminocyclohexanecarboxylic acid, 1-amino-3-methylcyclohexanecarboxylic acid and their monoalkylammonium salts.

Accordingly, the present invention also relates to a method of protecting plants from fungal attack, by treating the plants, the parts of the plant, or the site where it grows with a fungicidally effective amount of a 1-aminocyclohexanecarboxylic acid derivative of the formula I or Ia to Ig. An important field of application here is the treatment of the propagation stock for the protection from microorganisms, in particular of the seed, this also including those methods in which treated or even untreated seed is placed in a medium which has been pretreated with compounds of the formula I, for example into the seed furrow ("drench application").

The invention equally relates to propagation stock of plants which have been dressed in this manner, in particular to dressed seed.

1-Aminocyclohexanecarboxylic acid derivatives of the formula I are known in some cases.

For example, 1-aminocyclohexanecarboxylic acid itself and analogs are proposed in U.S. Pat. No.

3,746,495 as pharmaceuticals of the gastrointestinal tract for treating ulcers.

JP-A2 73/11958 proposes 1-aminocyclohexanecarboxylic acid and its Na, K, Ca, Mg or sulfamic acid salt as a sweetener which is not poisonous and has sweetening power which is superior to that of saccharin and cyclamate. Preparations of the formula I are therefore entirely acceptable for warm-blooded species and therefore do not represent any danger for the end user or for uninvolved persons (for example children), even when used inexpertly or stored carelessly.

Compounds of the formula I can be prepared with ease using the Strecker synthesis for obtaining amino acids. [Houben-Weyl, "Methoden der organ. Chemie [Methods of Organic Chemistry]" XI/2, 269 (1958)]

The addition of aqueous hydrocyanic acid or of cyanide on the ketimine double bond of the derivative of the formula III which has been formed as an intermediate

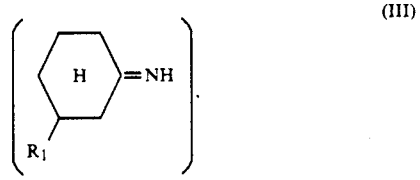

and which is the result of a reaction of the corresponding cyclohexanone derivative in the presence of ammonia, and hydrolysis of the 1-cyanocyclohexylamine formed, of the formula IV

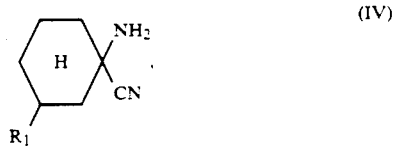

results in basic bodies which, if desired, can be converted into the corresponding esters, salts or metal complexes of the formula I in a customary manner.

Using another method, these basic bodies of the formula I can also be prepared by Bucherer Hydantoin synthesis under high pressure (about 5-20 atmospheres above atmospheric pressure) as follows:

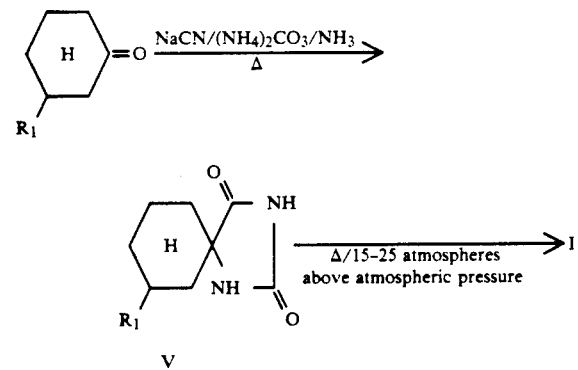

In this reaction, the corresponding cyclohexanone derivatives are reacted in the autoclave at increased temperature with alkali metal cyanide and ammonium carbonate in a solution in ammonia to give hydantoine derivatives of the formula V from which the 1-aminocyclohexanecarboxylic acid derivatives of the formula I are subsequently obtained by alkaline or acid hydrolysis [H. T. Bucherer, U. A.Lieb, J. prakt. Chemie, 141, 5 (1934)].

The intermediates of the formula V can be formed at 5 to 20 atmospheres above atmospheric pressure, preferably 8 to 12 atmospheres above atmospheric pressure, at temperatures from 80° to 150° C.

It may prove expedient to also carry out the hydrolysis of compounds of the formula V in the autoclave. As a rule, the process is carried out in the presence of an alkali metal hydroxide, for example sodium hydroxide or potassium hydroxide, at temperatures from 150° to 220° C. and pressures from 15 to 25 atmospheres above atmospheric pressure, preferably 17 to 20 atmospheres above atmospheric pressure.

The reaction can be carried out analogously to already known syntheses of cyclic aminocarboxylic acids, for example analogously to Journal of Medicinal Chemistry Vol. 16, No. 7, 823 (1973).

Surprisingly, it has now been found that 1-aminocyclohexanecarboxylic acid derivatives of the formula I have a microbicidal spectrum which is very favourable for the practical requirements of crop protection. Their main area of application is the control of harmful microorganisms, especially phytopathogenic fungi. Thus the compounds of the formula I have a very favourable curative, preventive and systemic action for protecting crop plants without influencing those by undesired side effects. Examples of crop plants which may be mentioned within the context of the present invention are: cereals (wheat, barley, rye, oats, rice); beet: (sugar beet and fodder beet); pomaceous fruit, stone fruit and soft fruit: (apples, pears, plums, peaches, almonds, cherries, strawberries, raspberries and blackberries); pulses: (beans, lentils, peas, soya); oil crops: (oilseed rape, mustard, poppy, olives, sunflowers, coconuts, castor, cocoa, peanuts); cucurbits: (pumpkin, cucumbers, melons); fibre plants: (cotton, flax, hemp, jute); citrus fruits: (oranges, lemons, grapefruit, tangerines); various vegetables: (spinach, lettuce, asparagus, cabbage species, carrots, onions, tomatoes, potatoes, capsicums), or plants such as maize, tobacco, nuts, coffee, sugar cane, tea, vines, hops, Musaceae and plants which yield natural rubber, and ornamental plants.

Using the active substances of the formula I, the microorganisms which occur on plants or parts of plants, (fruits, flowers, foliage, stalks, tubers, roots) of these and related crops can be restricted or destroyed, and parts of plants which grow later also remain free from such microorganisms. The active substances are active against the phytopathogenic fungi which belong to the following classes: Ascomycetes (for example Venturia); Basidiomycetes (for example Puccinia, Rhizoctonia); Fungi imperfecti (for example Cercospora); in particular against the Oomycetes which belong to the class of the Phytomycetes, such as Phytophthora, Bremia, Pseudoperonospora, Plasmopara or, for example Pythium. The compounds of the formula I also act against harmful bacteria, for example against the Xanthomonas species and Pseudomonas aeruginosa, which belong to the class of the Pseudomonadaceae and against other ubiquitous bacteria, for example Corynebacterium, Eschericia coli, Streptococcus and Staphylococcus species.

Compounds of the formula I have a systemic action. Besides, they can be employed with very good success as seed-dressing agents for treating seeds (fruits, tubers, grains) and plant cuttings as a protection against fungal infections, and against phytopathogenic fungi which occur in the soil.

The invention also relates to the novel compounds within the scope of the formula I and to microbicidal compositions which contain such compounds as active substances.

From amongst the low-molecular esters, these are the following compounds:
sec-butyl 1-aminocyclohexanecarboxylate,
isobutyl 1-aminocyclohexanecarboxylate,
ethyl 1-amino-3-methylcyclohexanecarboxylate,
n-propyl 1-amino-3-methylcyclohexanecarboxylate,
n-butyl 1-amino-3-methylcyclohexanecarboxylate,
sec-butyl 1-amino-3-methylcyclohexanecarboxylate,
isobutyl 1-amino-3-methylcyclohexanecarboxylate,
tert-butyl 1-amino-3-methylcyclohexanecarboxylate.

At the application rates conventionally used in crop protection and even at higher application rates, the compounds of the formula I are distinguished by outstandingly good plant compatibility, so that they protect crop plants from harmful microorganisms without adversely affecting their development.

To control these microorganisms, the compounds of the formula I can be used as pure substances or together with suitable carriers and/or other additives. Suitable carriers and additives can be solid or liquid and correspond to the substances conventionally used in the art of formulation, for example natural or regenerated mineral substances, solvents, dispersants, wetting agents, tackifiers, thickeners, binders or fertilizers. Active substances of the formula I can also be used as a mixture with other pesticidal or plant-growth-improving preparations. When applied to the soil, they themselves can also act simultaneously as trace-element sources when in the form of appropriate metal complexes.

In this context, the compounds of the formula I are employed together with the auxiliaries conventionally used in the art of formulation. For this purpose, they are expediently processed in a known manner to give, for example, emulsion concentrates, spreadable pastes, directly sprayable or dilutable solutions, dilute emulsions, wettable powders, soluble powders, dusts, granules, or encapsulations for example in polymeric substances. In the application methods such as spraying, misting, atomising, broadcasting, painting on or pouring, as well as the nature of the compositions, are selected to suit the intended aims and the prevailing circumstances. As a rule, favourable application rates are around 50 g to 5 kg of active ingredient (a.i.) per ha, preferably 100 g to 2 kg of a.i./ha, in particular around 200 g to 600 g of a.i./ha.

The formulations, i.e. the compositions, preparations or combinations containing the active substance of the formula I and, if desired, a solid or liquid additive, are prepared in a known manner, for example by intimately mixing and/or grinding the active substances with extenders, for example with solvents, solid carriers and, if desired, surface-active compounds (surfactants).

The following are possible as solvents: aromatic hydrocarbons, preferably the fractions $C_8$ to $C_{12}$, for example xylene mixtures or substituted naphthalines, phthalic esters such as dibutyl phthalate or dioctyl phthalate, aliphatic hydrocarbons, such as cyclohexane, or paraffins, alcohols and glycols as well as their ethers and esters, such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide, and also epoxidised or unepoxidised vegetable oils, such as epoxidised coconut oil or soya oil; or water.

Solid carriers which are generally used, for example for dusts and dispersible powders, are ground natural minerals such as calcite, talc, kaolin, montmorillonite or attapulgite.

Particularly advantageous additives which enhance application and which can lead to a substantial reduction of the amount applied, are furthermore natural phospholipids (of animal or vegetable origin) or synthetic phospholipids from the series of the kephalins and lecithins which can be obtained, for example, from soya beans.

Suitable surface-active compounds are non-ionic, cationic and/or anionic surfactants having good emulsifying, dispersing and wetting properties, depending on the nature of the active substance of the formula I to be formulated. Surfactants are also to be understood as meaning mixtures of surfactants.

Suitable anionic surfactants can be either so-called water-soluble soaps or water-soluble synthetic surface-active compounds.

Suitable soaps which may be mentioned are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids which can be obtained, for example, from coconut or tallow oil. Mention must also be made of the fatty acid methyl-laurates.

Non-ionic surfactants which are suitable are polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Examples of non-ionic surfactants which may be mentioned are nonylphenolpolyethoxyethanols, castor oil polyethylene glycol ethers, polypropylene/polyethylene oxide adducts, tributylphenoxpolyethyleneethanol, polyethylene glycol and octylphenoxypolyethoxyethanol.

Other suitable substances are fatty acid esters of polyoxyethylene sorbitan, such as polyoxyethylene sorbitan trioleate.

The cationic surfactants are mainly quaternary ammonium salts which contain at least one alkyl radical having 8 to 22 C atoms as N-substitutents and which have as further substituents lower halogenated or free alkyl, benzyl or lower hydroxyalkyl radicals.

Other surfactants conventionally used in the art of formulation are known to those skilled in the art or can be found in the specialist literature.

As a rule, the agrochemical preparations contain 0.1 to 99%, in particular 0.1 to 95%, of active substance of the formula I, 99.9 to 1%, in particular 99.9 to 5%, of a solid or liquid additive, and 0 to 25%, in particular 0.1 to 25%, of a surfactant.

While concentrated compositions are more preferred as commercial goods, the end user uses, as a rule, dilute compositions.

The active substance content in commercial compositions is between 0.1 and 90% by weight, preferably about 2 to 80% by weight, dilute compositions being more preferred by the user.

In the examples which follow, temperatures are given in degrees centigrade. Parts and percentages are based on weight.

PREPARATION EXAMPLES a) Preparation of the intermediate

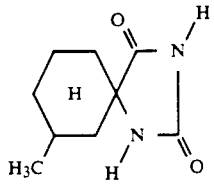

2-(3'-Methylcyclohexyl)-tetrahydroimidazolyl-3,5-dione

A mixture of 1 gmol of 3-methylcyclohexanone, 2,2 gmol of sodium cyanide, 1.5 gmol of ammonium carbonate, 2 liters of concentrated aqueous ammonia solution and 2 liters of ethanol are heated for 3 hours at 120° C. in the autoclavel, with stirring, the internal pressure rising to 12 atmospheres above atmospheric pressure. The ethanol is subsequently distilled off, the reaction mixture is cooled to room temperature and filtered. The residue is washed with water until free from salts and dried over phosphorus pentoxide. Yield: 86% (pale yellow crystals).

| Elemental analysis (in %): | | | |
|---|---|---|---|
| | C | H | N |
| calculated: | 59.33 | 7.75 | 15.38 |
| found: | 58.9 | 7.6 | 15.1 | b) Preparation of the End Product

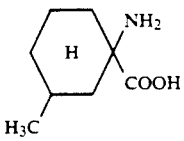         (6)

1-Amino-3-methylcyclohexancarboxylic acid 1 gmol of 2-(3'-methylcyclohexyl)-tetrahydroimidazolyl-3,5-dione which has been prepared following a) is heated in 3.9 liters of 1.25 -normal aqueous sodium hydroxide solution in the autoclave for 2 hours at 195° C., with stirring; during this process the internal pressure rises to 20 atmospheres above atmospheric pressure. The reaction solution is subsequently cooled to room temperature, diluted with 2 liters of water, and brought to a pH of about 1-2 using hydrochloric acid, during which process small amounts of resinous flocculations occur which are filtered off. The filtrate is now brought to a pH of 6-7 using aqueous sodium hydroxide solution, concentrated to ⅓ of the volume and cooled with ice-water. The crude product is filtered off and portions of it are washed with cold water until free from salts. Yield 92%. (colourless crystals)

| Elemental analysis (in %): | | | |
|---|---|---|---|
| | C | H | N |
| calculated: | 61.1 | 9.6 | 8.9 |
| found: | 61.4 | 9.5 | 8.3 |

EXAMPLE 2

Preparation of the Metal Complex

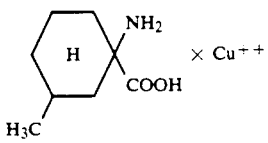

Copper complexes of 1-aminocyclohexanecarboxylic acid 1 part of 1-aminocyclohexanecarboxylic acid is dissolved in 20 parts of water. 3 parts of copper (II) acetate in form of a 10% aqueous solution are added dropwise to this solution. The mixture is stirred for about 4 days at room temperature. The copper complex which has precipitated is filtered off, washed with a little water and dried. Yield 70% of theory.

EXAMPLE 3

Preparation of

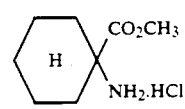         (24)

Methyl 1-aminocyclohexanecarboxylate 1 g of aminocyclohexanecarboxylic acid is suspended in 20 ml of methanol. HCl gas is passed in for 1 minute, during which process the temperature rises to 40° C. The solution, which is now clear, is refluxed overnight. The methanol is subsequently removed under reduced pressure, another 10 ml of methanol are added to the solid, and the solvent is again removed under reduced pressure. The solid is digested with ether (2×10 ml) and dried. The title compound of melting point 206°-207° C. is obtained.

The following compounds of the formula I can be prepared analogously or following one of the methods indicated further above.

TABLE 1

| Comp. No. | $R_1$ | $R_2$ | Complex or salt | Elemental analysis calc./found | $^1$H-NMR ($\delta$) or other physical constant. |
|---|---|---|---|---|---|
| 1 | H | H | — | C: 58.7/57.5% H: 9.1/8.9% N: 9.8/9.6% | m.p. >250° C. |
| 2 | H | H | $H_2SO_4$ | | |
| 3 | H | H | Zn | | m.p. >200° C. |

TABLE 1-continued

| Comp. No. | R₁ | R₂ | Complex or salt | Elemental analysis calc./found | $^1$H-NMR ($\delta$) or other physical constant. |
|---|---|---|---|---|---|
| 4 | H | H | $H_2N-C_2H_5$ | | |
| 5 | H | H | Ca | | |
| 6 | $CH_3$ | H | — | C: 61.1/61.4% H: 9.6/9.5% N: 8.9/8.3% | Solvent $CD_3OD$ $CH_3$: 0.9 (d, 5Hz, 3H) cyclo $C_6H_9$: 0.85-2.3 (m, 9H) $H_2O$, $NH_2$: 4.87 |
| 7 | $CH_3$ | H | $H_2N$-iso$C_3H_7$ | — | Solvent.: $D_2O$ $CH_3$: 1,2 (d, $J_{CH}$6Hz, 3H) cyclo $C_6H_9$: 1.1-2.5 (m, 9H) $C(CH_3)_2$: 1.62 (d, $J_{CH}$6Hz, 6H) $H_2O$, $NH_2$: 4.96 |
| 8 | $CH_3$ | H | Cu | C: 43.5/43.2% H: 6.8/7.1% N: 6.3/6.0% Cu: 28.7/28.5% | |
| 9 | H | $C_2H_5$ | — | | $n_D^{21} = 1.4606$ |
| 10 | H | $CH_3$ | — | | b.p. 60-64°/1 mbar |
| 11 | $C_2H_5$ | $CH_3$ | $HNO_3$ | | |
| 12 | tert-$C_4H_9$ | H | — | | |
| 13 | H | iso$C_3H_7$ | — | | b.p. 55-58°/0,07 mbar |
| 14 | H | benzyl | — | | |
| 15 | H | n$C_6H_{13}$ | — | | |
| 16 | H | H | Na/K | | m.p. >250° C. |
| 17 | H | H | Cu/Ni/Mn | | m.p. >200° C. |
| 18 | H | H | Fe | | m.p. >280° C. |
| 19 | H | H | $H_2N$-benzyl | | |
| 20 | H | H | $N(CH_3)_2$phenyl | | m.p. >180° C. |
| 21 | H | H | $N(C_2H_5)_2$benzyl | | m.p. >180° C. |
| 22 | H | H | $H_2N-C_{12}H_{23}n$ | | |
| 23 | H | H | Mn | | m.p. >250° C. |
| 24 | H | $CH_3$ | HCl | | m.p. 206-207° C. |
| 25 | $CH_3$ | $CH_3$ | HCl | | m.p. 190-200° C. |

| 2.1. Wettable powder | a | b | c |
|---|---|---|---|
| Active substance from Table 1 | 25% | 50% | 75% |
| Na ligninsulfonate | 5% | 5% | — |
| Na lauryl sulfate | 3% | — | 5% |
| Na diisobutylnaphthaline sulfonate- | — | 6% | 10% |
| Octylphenol polyethylene glycol ether (7-8 mol ethylene oxide) | — | 2% | — |
| Highly-disperse silica | 5% | 10% | 10% |
| Kaolin | 62% | 27% | — |

The active substance is mixed with the additives and thoroughly ground in a suitable mill. This gives wettable powder which can be diluted with water to give suspensions of any desired concentration.

| 2.2. Emulsion concentrate | |
|---|---|
| Active substance from Table 1 | 10% |
| Octylphenol polyethylene glycol ether (4-5 mol of ethylene oxide) | 3% |
| Ca dodecylbenzenesulfonate | 3% |
| Castor oil polyglycol ether (35 mol of ethylene oxide) | 4% |
| Cyclohexanone | 34% |
| Xylene mixture | 50% |

Emulsions of any desired concentration can be prepared from this concentrate by diluting it with water.

| 2.3. Dusts | a | b |
|---|---|---|
| Active substance from Table 1 | 5% | 8% |
| Talc | 95% | — |
| Kaolin | — | 92% |

Ready-to-use dusts are obtained by mixing the active substance with the carrier and grinding the mixture on a suitable mill.

| 2.4. Extruder granules | |
|---|---|
| Active substance from Table 1 | 10% |
| Na ligninsulfonate | 2% |
| Carboxymethylcellulose | 1% |
| Kaoline | 87% |

The active substance is mixed with the additives, and the mixture is ground and moistened with water. This mixture is extruded and subsequently dried in a stream of air.

| 2.5. Coated granules | |
|---|---|
| Active substance from Table 1 | 3% |
| Polyethylene glycol (MW 200) | 3% |
| Kaolin | 94% |

(MW = molecular weight)

The kaolin is moistened with polyethylene glycol and the finely ground active substance is applied uniformly thereto in a mixer. Dust-free coated granules are obtained in this manner.

| 2.6. Suspension concentrate | |
|---|---|
| Active substance from Table 1 | 40% |
| Ethylene glycol | 10% |
| Nonylphenol polyethylene glycol ether (15 mol) of ethylene oxide) | 6% |
| Na ligninsulfonate | 10% |
| Carboxymethylcellulose | 1% |
| 37% aqueous formaldehyde solution | 0.2% |
| Silicon oil in the form of a 75% aqueous emulsion | 0.8% |
| Water | 32% |

The finely-ground active substance is mixed intimately with the additives. This gives a suspension concentrate from which suspensions of any desired concentration can be prepared by diluting it with water.

3. BIOLOGICAL EXAMPLES

Example 1

Action against Phytophthora Infestans on Tomato Plants a) Residual-Protective Action Tomato plants are grown for 3 weeks and then sprayed with a spray liquor prepared with a wettable powder of the active substance (0.02% of active ingredient). After 24 hours, the treated plants are infected with a sporangia suspension of the fungus. Fungal attack is assessed after the infected plants have been incubated for 5 days at 90–100% relative atmospheric humidity and 20° C.

Compared with untreated control plants (100% attack), plants which had been treated with one of the compounds Nos. 1, 3, 6, 7, 8, 10, 13, 16, 17, 18, 23, 24 or 25 showed less than 10% or no attack.

b) Residual-Curative Action

Tomato plants are grown for 3 weeks and then infected with a sporangia suspension of the fungus. After the infected plants have been incubated for 22 hours in a humid chamber at 90–100% relative atmospheric humidity and 20° C., they are dried and sprayed with a spray liquor prepared with a wettable powder of the active substance (0.02% of active ingredient). After the spray coating has dried on, the treated plants are retransferred to the humid chamber. Fungal attack is assessed 5 days after the infection.

Compared with untreated control plants (100% attack), tomato plants which had been treated with a spray liquor containing one of the compounds Nos. 1, 6, 7, 8, 10, 13, 17, 18 showed less than 10% fungal attack.

c) Systemic Action

Tomato plants are grown for 3 weeks and a spray liquor prepared with a wettable powder of the active substance (0.006% of active ingredient based on the soil volume) is then poured on. Care is taken that the spray liquor does not come in contact with the aerial parts of the plant. After 48 hours, the treated plants are infected with a sporangia suspension of the fungus. The fungal attack is assessed after the infected plants have been incubated for 5 days at 90–100% relative atmospheric humidity and 20° C.

In the above test, the following compounds, inter alia, showed a very good systemic action: Nos. 1, 3, 6, 7, 8, 10, 13, 16, 17, 18, 20, 21 or 23. Compared with untreated control plants (100% attack), these compounds caused complete suppression of fungal attack.

Example 2

Action Against Mould on Moist Maize

Dry maize kernels (80 g samples) are placed in sealable plastic beakers and thoroughly mixed with the test substance in the form of an aqueous suspension, emulsion or solution. The application rate of the substance is chosen so that a concentration of 0.06% of a.i., based on the dry maize weight, is achieved. A moistened paper tissue provides a moisture-saturated atmosphere in the beakers which are filled with maize and subsequently sealed. After the maize samples have been incubated for 2–3 weeks at about 20° C., those treated only with water spontaneously develop a mixed population of moulds. Artificial infection was superfluous. The inhibition of fungal development after 3 weeks was used for assessing the effectiveness of the test substance.

Compared with untreated maize kernels (control with 100% attack), kernels which had been treated with compounds of the formula I showed that fungal attack was effectively inhibited. Compounds Nos. 1 and 7 even completely suppressed development of the moulds.

What is claimed is:

1. A method of protecting plants from fungal attack, which comprises treating the plants, the parts of the plant or the site where it grows with a fungicidally effective amount of a 1-aminocyclohexanecarboxylic acid derivative having the formula I,

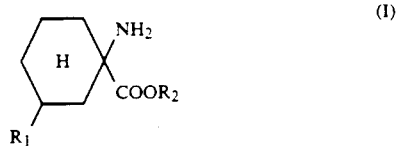

an acid addition salt or a metal complex thereof, $R_1$ being hydrogen, methyl, ethyl or isopropyl and $R_2$ being hydrogen, methyl, ethyl, propyl, isopropyl, the metal ion equivalent of Li, Na, K, Mg, Ca, Cu, Mn, Zn, Sn, Fe, Ni, Co, Cr, Al, Ti, Zr or of two or more of these elements.

2. A method according to claim 1, wherein $R_2$ is hydrogen or one, two or more of the metal ion equivalents mentioned.

3. A method according to claim 2, wherein $R_1$ is hydrogen.

4. A method according to claim 3, wherein $R_2$ is hydrogen.

5. A method according to claim 2, wherein $R_1$ is methyl.

6. A method according to claim 5, wherein $R_2$ is hydrogen.

7. A method according to claim 1, wherein the propagation stock of the plant is treated.

8. A method according to claim 1, which comprises placing seed in a medium which has been pretreated with an active substance of the formula I.

* * * * *